US00PP36601P2

(12) United States Plant Patent
van Haaster

(10) Patent No.: US PP36,601 P2
(45) Date of Patent: Apr. 15, 2025

(54) ***DAHLIA* PLANT NAMED 'DDAHCHPCHP'**

(50) Latin Name: ***Dahlia* hybrid**
Varietal Denomination: DDAHCHPCHP

(71) Applicant: Ans van Haaster, Hillegom (NL)

(72) Inventor: Ans van Haaster, Hillegom (NL)

( * ) Notice: Subject to any disclaimer, the term of this patent is extended or adjusted under 35 U.S.C. 154(b) by 0 days.

(21) Appl. No.: 18/896,970

(22) Filed: Sep. 26, 2024

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./263.1, 321
See application file for complete search history.

(56) References Cited

U.S. PATENT DOCUMENTS

PP28,223 P3 * 7/2017 Uchneat ..... Plt./321

* cited by examiner

*Primary Examiner* — Karen M Redden
(74) *Attorney, Agent, or Firm* — Cassandra Bright

(57) ABSTRACT

A new and distinct cultivar of *Dahlia* plant named 'DDAHCHPCHP' is disclosed, characterized by abundant peach and white colored decorative type flowers, dark green foliage, and a mounded habit. The new variety is a *Dahlia*, typically produced as an ornamental plant.

2 Drawing Sheets

Figure 1:
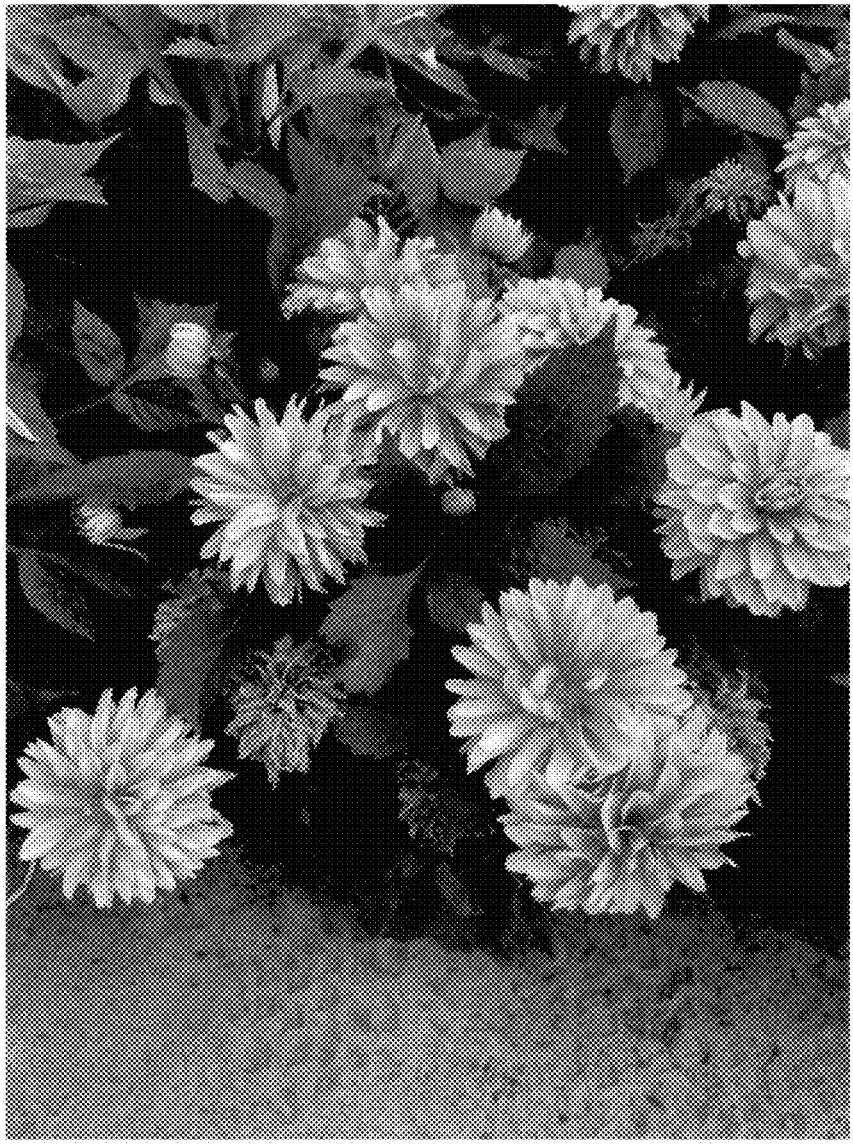

Latin name of the genus and species: *Dahlia* hybrid.
Variety denomination: 'DDAHCHPCHP'.

BACKGROUND OF THE INVENTION

The new *Dahlia* cultivar is a product of a planned breeding program conducted by the inventor, Ans van Haaster in Hillegom, the Netherlands. The objective of the breeding program was to produce useful new *Dahlia* varieties for ornamental horticultural production. The crossing resulting in this new variety was made in August 2020.

The seed parent is the unpatented variety *Dahlia* 'Hypnotica White', unpatented. The pollen parent is the unpatented variety *Dahlia* 'Hypnotica Rose Bicolor', unpatented. The new variety was discovered in August 2021 by the inventor in a group of seedlings in Hillegom, the Netherlands. Asexual propagation of *Dahlia* was performed by vegetative cuttings in September 2021, at the same location in Hillegom, the Netherlands. After selection of the new variety, extensive confidential testing has been performed to determine and define the desirable characteristics of the new variety.

SUMMARY OF THE INVENTION

The cultivar 'DDAHCHPCHP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DDAHCHPCHP'. These characteristics in combination distinguish 'DDAHCHPCHP' as a new and distinct *Dahlia* cultivar:

1. Abundant flower production.
2. Mature flowers are colored light pink and peach.
3. Decorative type *Dahlia* flowers.

PARENT COMPARISONS

Plants of 'DDAHCHPCHP' are similar in some horticultural characteristics to the seed parent. The new variety, however, differs in the following:

1. Plants of the new variety are more compact than plants of the seed parent.
2. Flower color of the new variety is light pink and peach, while flower color of the seed parent is white.

Plants of 'DDAHCHPCHP' are similar in some horticultural characteristics to the pollen parent. The new variety, however, differs in the following:

1. Plants of the new variety are more compact than plants of the pollen parent.
2. Flower color of the new variety is light pink and peach, while flower color of the pollen parent is yellow and light pink.

COMMERCIAL COMPARISONS

Plants of 'DDAHCHPCHP' are similar in some horticultural characteristics to the variety *Dahlia* 'Dalina Maxi Peach', unpatented. The new variety, however, differs in the following:

1. Flower color of the new variety is light pink and peach, while flower color of this comparator is peach and pink.
2. Foliage color of the new variety is lighter than foliage color of this comparator.
3. Flowers of the new variety have fewer petals than flowers of this comparator.

Plants of 'DDAHCHPCHP' are similar in some horticultural characteristics to the variety *Dahlia* 'Bahama Apricot', unpatented. The new variety, however, differs in the following:

1. Central flower color of the new variety is light pink and peach, while the central flower color of this comparator is peach with white edges.
2. Flower stems of the new variety are shorter than flower stems of this comparator.
3. Leaf margins of the new variety are more serrated than leaf margins of this comparator.

BRIEF DESCRIPTION OF THE PHOTOGRAPHS

The accompanying photograph in FIG. 1 illustrates in full color a typical plant of 'DDAHCHPCHP' 64 days from planting, grown in a 15 cm pot.

Figure 2:
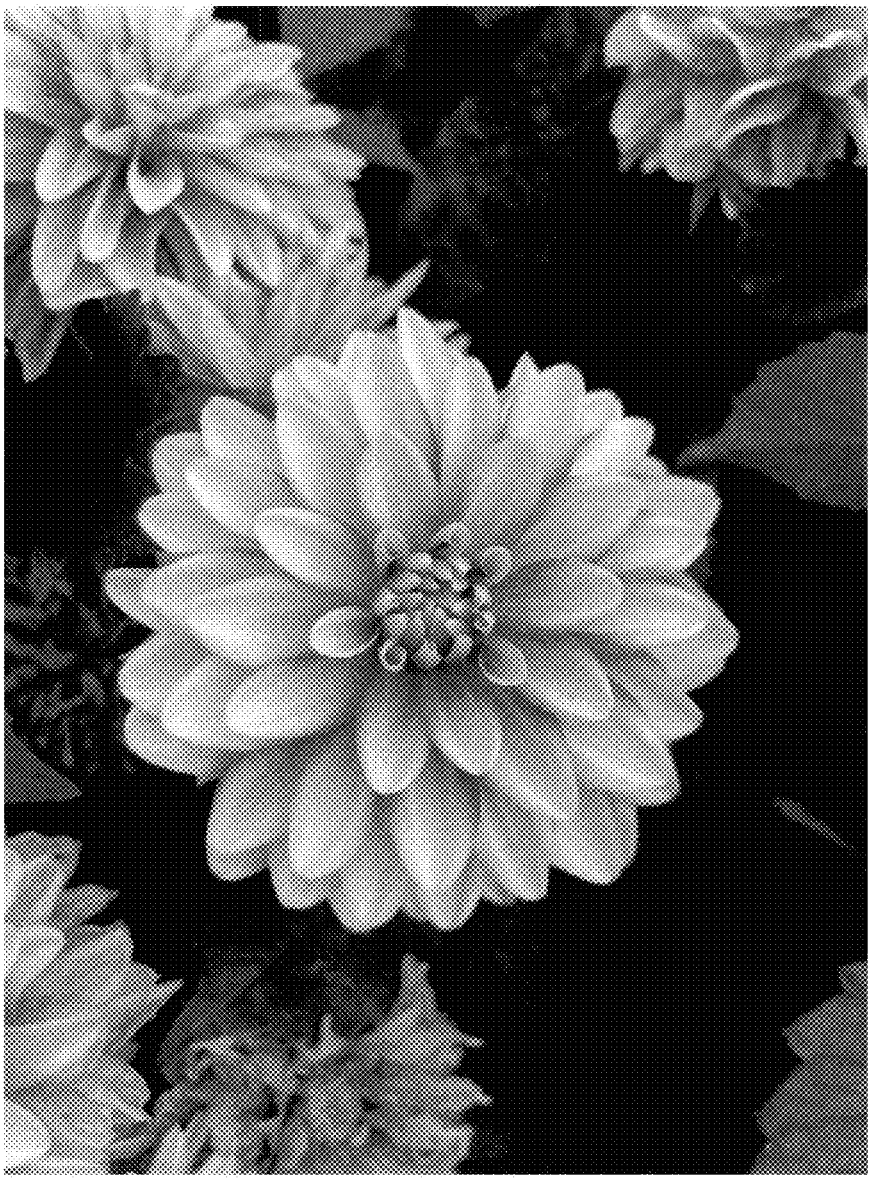

FIG. 2 illustrates a closer view of a typical flower of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DDAHCHPCHP' plants grown in a plastic tunnel in Hillegom, the Netherlands, under natural lighting. Measurements were taken August 2024. The growing temperature ranged from approximately 15° C. to 32° C. during the days, 8° C. to 20° C. during the nights. Measurements and numerical values represent averages of typical plant types.

Botanical classification: *Dahlia* hybrid 'DDAHCHPCHP'.

PROPAGATION

Propagation method: Vegetative cuttings.
Time to initiate rooting: 8 to 15 days in summer; 12 to 17 days in winter.
Root description: Fibrous and relatively shallow in the early stages of development. Roots grow more complex as the plant matures.
Tuber description: Skin firm and relatively thin, colored light brown (199A). Inner flesh moist and firm, colored white (155A).

PLANT

Age of plant described: Approximately 64 days from a rooted cutting.
Growth habit: Mounded.
Height: 36 cm.
Plant spread: 45 cm.
Branching characteristics: Very well branched.
Quantity of lateral branches: 10 per main stem.
Characteristics of primary lateral branches:
- *Length.*—14 cm.
- *Diameter.*—0.5 cm.
- *Color.*—RHS Yellow-Green 145A.
- *Texture.*—Smooth.
- *Strength.*—Medium.

Internode length: 8 cm.

FOLIAGE

Leaf:
- *Arrangement.*—Alternate.
- *Quantity.*—Approximately 5 per branch.
- *Average length.*—16 cm.
- *Average width.*—16 cm.
- *Pubescence.*—None.
- *Shape.*—Triangle.
- *Apex.*—Acuminate.
- *Base.*—Rounded, slightly cordate.
- *Margin.*—Serrate.
- *Texture.*—Smooth, both sides.
- *Aspect.*—Nearly flat.
- *Color.*—Young, Upper side: RHS Green 137B. Young, Under side: RHS Green 138B. Mature, Upper side: RHS Green 137B. Mature, Under side: RHS Green 138B.
- *Venation.*—Pattern: Reticulate. Color, upper side: RHS Green 138B. Color, under side: RHS Green 138B.

Petiole:
- *Length.*—5 cm.
- *Diameter.*—0.5 cm.
- *Color.*—RHS Yellow-Green 145A.
- *Texture.*—Smooth.

Stipule:
- *Length.*—3 cm.
- *Diameter.*—1 cm.
- *Color.*—RHS Green 138B.
- *Texture.*—Smooth.

FLOWER

Natural flowering season: Summer to autumn.
Days to flowering from rooted cutting: 49 days.
Inflorescence and flower type and habit: Decorative *Dahlia* type.
Rate of flower opening: 7 to 12 days from bud to fully opened flower.
Flower longevity on plant: 20 days.
Persistent or self-cleaning: Persistent.

Bud:
- *Shape.*—Round.
- *Length.*—1.5 cm.
- *Diameter.*—2.5 cm.
- *Color.*—RHS Green 138C.

Flower size:
- *Diameter.*—10 cm.
- *Depth.*—5 cm.

Petals:
- *Arrangement.*—Double flower, radial symmetry.
- *Length.*—4 cm.
- *Width.*—1.5 cm.
- *Quantity.*—96.
- *Texture.*—Smooth.
- *Apex.*—Round.
- *Base.*—Pointed.
- *Shape.*—Oval.
- *Margin.*—Entire.
- *Color.*—When Opening, Upper Surface: RHS Greyed-Orange 171B basal section, fading to Purple 76C towards apex. When Opening, Lower Surface: RHS Greyed-Red 182A basal section, fading to Purple 76B towards apex. Fully Opened, Upper Surface: RHS Greyed-Orange 170B basal section, fading to Purple 75D towards apex. Fully Opened, Lower Surface RHS Greyed-Red 181C basal section, fading to Purple 75D towards apex.

Sepals:

*Quantity per flower.*—6.

*Shape*.—Oval.

*Length.*—1.5 cm.

*Width.*—0.7 cm.

*Apex*.—Round.

*Base*.—Pointed.

*Margin*.—Entire.

*Color*.—RHS Green 138A.

Peduncles: None.

Fragrance: Soft.

REPRODUCTIVE ORGANS

Androecium:

Stamens:

*Number.*—48.

Anthers:

*Shape*.—Elongated, narrow.

*Length*.—About 0.5 cm.

*Color*.—RHS Yellow-Orange 17A.

*Pollen*.—Color: RHS Yellow-Orange 17A. Quantity: Abundant.

Gynoecium:

Pistil:

*Number.*—48.

*Length.*—1 cm.

*Style*.—Shape: V-shaped. Length: 1.5 cm. Color: RHS Yellow-Orange 17C.

*Stigma*.—Shape: V-shaped. Color: RHS Yellow-Orange 17C. Ovary Color: RHS Yellow-Orange 17C.

OTHER CHARACTERISTICS

Seeds and fruits: Not observed.

Disease/pest resistance: Neither resistance nor susceptibility to typical *Dahlia* pests and diseases observed.

Temperature tolerance: Tolerates temperatures from 1° to 38° C.

What is claimed is:

1. A new and distinct cultivar of *Dahlia* plant named 'DDAHCHPCHP' as herein illustrated and described.

* * * * *